United States Patent [19]

Green et al.

[11] Patent Number: 5,212,293
[45] Date of Patent: May 18, 1993

[54] PROCESS FOR THE PREPARATION OF DEOXYNUCLEOSIDES

[75] Inventors: Kenneth E. Green, Yorktown Heights, N.Y.; John L. Considine, Jr., Bridgewater, N.J.; Joseph D'Antuono, III, Three Bridges, N.J.; Thurairajah Padmanathan, Piscataway, N.J.

[73] Assignee: American Cyanamid Company, Wayne, N.J.

[21] Appl. No.: 941,357

[22] Filed: Sep. 4, 1992

Related U.S. Application Data

[63] Continuation of Ser. No. 563,596, Aug. 6, 1990, abandoned.

[51] Int. Cl.$^5$ .............................................. C07H 1/00
[52] U.S. Cl. .................................. 536/28.2; 536/120
[58] Field of Search ................................. 536/23, 120

[56] References Cited

U.S. PATENT DOCUMENTS 3,775,397  11/1973  Etzold et al. .......................... 536/23

FOREIGN PATENT DOCUMENTS 0268475  5/1989  Fed. Rep. of Germany .

OTHER PUBLICATIONS

Etzold, G. et al., Tetrahedron, (1971) 27: 2463–2742.
Kowallik, V. G. et al., J. F. Prakt. Chemie., (1973) 315: 895–900.
Herdewijn, P. et al., J. Med. Chem., (1987) 30: 1270–1278.
Van Aerschot, A. et al., J. Med. Chem., (1979) 32: 1743–1749.

*Primary Examiner*—Johnnie R. Brown
*Assistant Examiner*—J. Oliver Wilson
*Attorney, Agent, or Firm*—Kenneth J. Dow

[57] ABSTRACT

An improved process for the preparation of 2′ and 3′-(halo-substituted)-2′,3′-dideoxy nucleosides by reacting a protected anhydrothymidine compound with a halogenating composition containing a substituted organo-aluminum compound which exhibits greater solubility in conventional solvents than AlF$_3$.

40 Claims, No Drawings

PROCESS FOR THE PREPARATION OF DEOXYNUCLEOSIDES

This is a continuation of co-pending application Ser. No. 07/563,596, filed on Aug. 6, 1990, now abandoned.

BACKGROUND OF THE INVENTION

1. Field of the Invention

The present invention is directed to a novel process for the synthesis of 3'-(halo-substituted)2',3'-dideoxynucleosides and 2'-(halo-substituted)2',3'-dideoxynucleosides from the corresponding anhydro-dideoxynucleoside counterparts.

2. Description of the Prior Art

Acquired Immunodeficiency Syndrome (AIDS), recognized as a systemic immunosuppressive disorder, is an infectious disease caused by a retrovirus termed human immunodeficiency virus (HIV). Since HIV is a retrovirus, viral reverse transcriptase appears to be a selective target for antiviral agents. Accordingly, a number of different reverse transcriptase inhibitors having different chemical structures have been reported to be active against HIV replication in vitro and in vivo.

Of these reverse transcriptase inhibitors, the 2',3'-dideoxyribonucleosides in particular are reported to have significant inhibitory activity against HIV in vitro (R. Dagani, Chem. and Eng. News, 41-49, Nov. 23, 1987; E. De Clercq, A. Van Aerschot, P. Herdewijn, M. Baba, R. Pauwels and J. Balzarini Nucleosides and Nucleotides, 8 (5 and 6), 659-671 (1989); A. Van Aerschot, P. Herdewijn, J. Balzarini, R. Pauwels and E. De Clercq, J. Med. Chem. 32, 1743-1749 (1989)).

Among the 2',3'-dideoxyribonucleoside products reported, 3'-azido-2',3'-dideoxythymidine (AZT), and 3'-deoxy-3'-fluorothymidine (also referred to as 2',3'-dideoxy-3'-fluorothymidine or FLT) in particular show selective anti-HIV-1 activity. The compound 3'-azido-2',3'-dideoxythymidine (AZT) is being sold commercially as a potent inhibitor of HIV-induced cytopathogenicity. However, 3'-deoxy-3'-fluorothymidine is reported to have increased activity over AZT (Balzarini, J., et al., Biochem. Pharmacol. 1988, 37, 2847; P. Herdewijn, J., et al., J. Med. Chem. 30, 1270-1278 (1987)). Accordingly, the compound 3'-deoxy-3'-fluorothymidine (FLT) and other 2' or 3'-fluoro-substituted deoxynucleosides are in particular interest as possible agents for the treatment for AIDS.

However, researchers have encountered several problems in preparing fluorinated nucleosides, including: (1) very low productivity in the existing methods of fluorination which require low concentrations of reagents and substrate and (2) minimal solubility of existing reagents in solvents normally used in the process of fluorination; and (3) inconsistent results obtained when some of the prior art processes are used.

The synthesis of FLT is known from G. Etzold, R. Hintsche, G. Kowollik and P. Langen, Tetrahedron 27 (1971) pp. 2463-2472. They describe the reaction of 2,3'-Anhydro-1-(2-deoxy-β-D-xylofuranosyl)thymine with HF using AlF$_3$ as a catalyst at 150°-170° to obtain the product at 28% yield. They also describe its preparation by the reaction of 3'-O-mesyl-thymidine with KHF$_2$ or NH$_4$F at 190° to obtain the product at 14% yield. In another reference, the authors synthesized 3'-deoxy-3'-fluorothymidine from 2,3'-anhydro-1-(2-deoxy-5-O-mesyl-β-D-threo-pentofuranosyl)thymine using HF-AlF$_3$. (J. Prakt. Chem., 315, 895 (1973).

In U.S. Pat. No. 3,775,397 the same authors report the preparation of 3'-deoxy-3'-fluorothymidine by heating the 2,3'-anhydro-1-(2-deoxy-β-D-xylofuranosyl)thymine with 30 cm.$^3$ of a 4-6% solution of HF in anhydrous dioxane in a sealed vessel at 90° C. to obtain the product at yields of up to 46%. Attempts to reproduce this procedure by the present inventors have not produced any appreciable amounts of the product, however.

Other closely related compounds have been fluorinated using diethylaminosulfur trifluoride (DAST). (See A. Van Aerschot, P. Herdewijn, J. Balgarini, R. Pauwels and E. DeClerq., J. Med. Chem. 32, 1743-1749 (1989))

All of these prior art references are directed to laboratory scale synthesis of the subject compounds. Attempts to produce the compounds for large scale manufacture according to the prior art procedures have proven to be unsatisfactory, however. The productivity of the prior art reactions is impractical for large scale manufacture. Very dilute concentrations of fluorinating reagents and large volumes (e.g. 0.5-1.0% for AlF$_3$) are required as well as high temperatures due to the low solubility of the reagents. In addition, the disclosed reactions generally give rise to unisolated contaminates. Moreover, difficulties have been encountered in obtaining consistent, appreciable yields using the methods of the prior art. Reported yields with AlF$_3$/HF or with KHF$_2$ or NH$_4$F are particularly difficult to reproduce on a consistent basis. Also, the use of some of the reagents pose a safety hazard, particularly for large scale manufacture (e.g. DAST). As a result of these problems, the prior art procedures are not well suited for large scale manufacture of the compounds of the present invention.

Accordingly, there is a need for a method of producing 2' and 3'-(fluoro-substituted)dideoxynucleosides suitable for large scale manufacture, which method circumvents the reagent solubility problems and produces good yields of the products in a consistently reproducible manner.

Surprisingly, it has been discovered that the use of a substituted organo aluminum reagent of the formula:

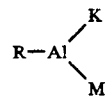

wherein R, K and M are as defined below, results in a marked improvement in the productivity, yield, and operability of the reaction. In addition, a highly pure product is obtained without the need for further processing, such as chromatography. The use of the substituted organo aluminum reagent of the present invention allows the reaction to be carried out with smaller volumes and a lower temperature thereby resulting in good, consistently reproducible yields of the 2' or 3'-(fluoro-substituted)dideoxynucleosides.

SUMMARY OF THE INVENTION

This invention embodies the general concept of using substituted organo aluminum compounds, which are more soluble in organic solvents than their inorganic counterparts, to enhance the ability of nucleophiles to be substituted on nucleosides.

In particular, this invention is directed to an improved process for preparing 3'-(halo-substituted)-2',3'-dideoxynucleosides and 2'-(halo-substituted)2',3'-dideoxynucleosides by reacting a protected anhydrothymidine compound with a halogenating composition containing a substituted organoaluminum compound which exhibits greater solubility in conventional solvents than AlF₃.

More specifically, the invention is directed to an improved process for preparing 2' or 3'-(halo-substituted)-2',3'-di-deoxynucleosides selected from those of formulae:

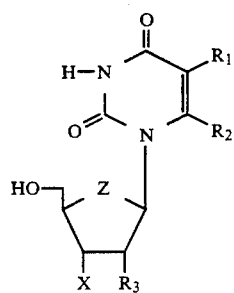

(I)

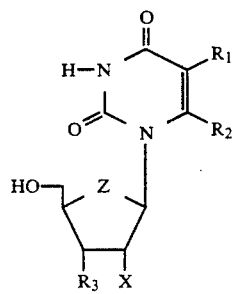

(II)

wherein Z is oxygen or CH₂;

$R_1$ and $R_2$ may be the same or different and are selected from hydrogen, lower alkyl, halogen, olefinic, aryl and substituted aryl;

$R_3$ is selected from hydrogen and halogen; and X is a halogen;

which process comprises the steps of:

(A) reacting a compound of Formula (1a) or (1b)

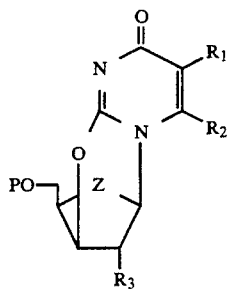

(1a)

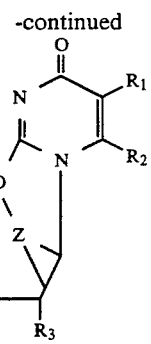

(1b)

wherein $R_1$, $R_2$, and $R_3$ are as hereinbefore defined and P is hydrogen or a suitable protecting group which may be selected from those consisting of triphenylmethyl, methoxytriphenylmethyl, acetyl, pivaloyl, methanesulfonyl or trialkyl-silyl with a reagent of the formula:

H-X wherein X is a halogen in the presence of an additional reagent of the formula:

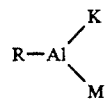

wherein R is selected from the group consisting of (C₁–C₁₂) branched or unbranched alkyl, (C₁–C₁₂) branched or unbranched alkoxy, phenoxy or substituted phenoxy, phenyl or substituted phenyl, hydrogen, carboxylate, benzyl, enolate, β-diketonate, carbonyl, olefin, (C₁–C₁₂) branched or unbranched thioalkyl, thiophenyl or substituted thiophenyl; K and M may be the same or different and may be selected from the same group as R or a halogen; to yield a protected intermediate of the Formula (2a) or (2b),

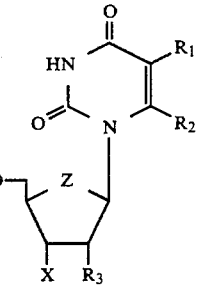

(2a)

(2b)

and then (B) where P is other than hydrogen, removing the protecting group P to give the 3'-(halo-substituted)2',3'-dideoxynucleosides or 2'-(halo-substituted)2',3'-dideoxynucleosides. When P is hydrogen, removal of the protecting group P is unnecessary.

DETAILED DESCRIPTION OF THE INVENTION

The process for preparing the 2' or 3'-(halo-substituted)2',3'-dideoxynucleosides may conveniently be summarized by the following reaction sequence of Scheme I.

In this reaction, the protected anhydronucleoside (1a) or (1b), is reacted in Step (A) to give the protected substituted nucleosides (2a) or (2b) which can then be converted in Step (B) to the deprotected 3'-(substituted)2',3'-dideoxynucleoside (3a) and the 2'-(substituted)2',3'-dideoxynucleoside (3b) by reported procedures. Scheme I is as follows:

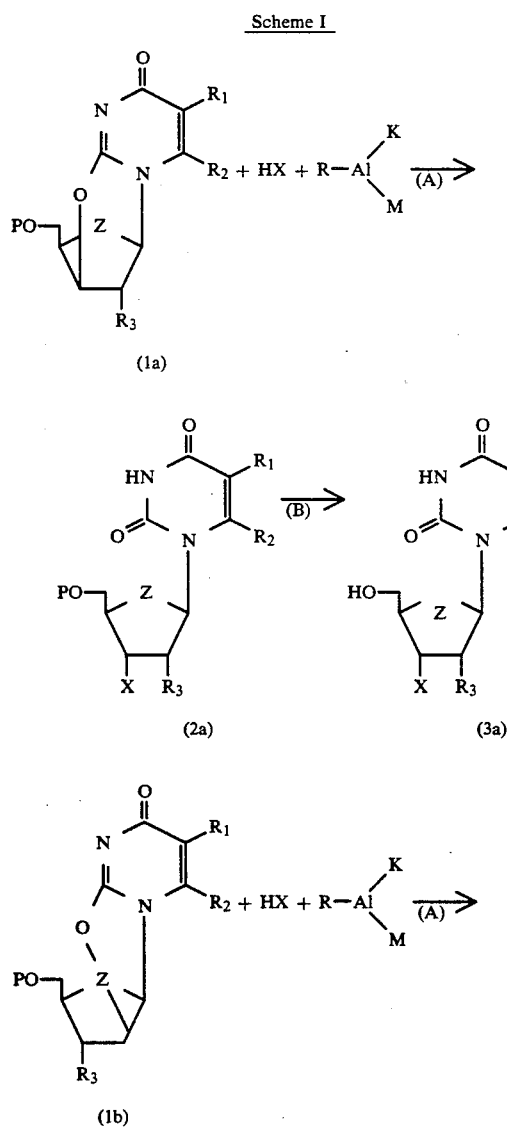

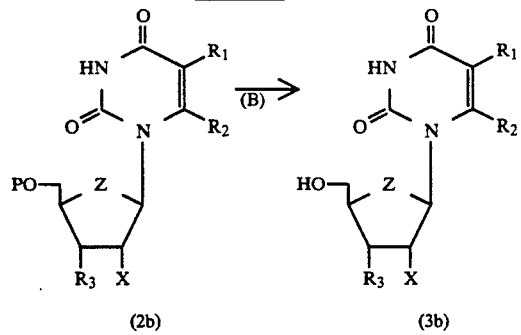

Referring to Scheme I, Step (A) illustrates the reaction between an appropriately substituted reagent H-X and an anhydronucleoside (1a) or (1b) in the presence of the substituted organoaluminum reagent to form the protected substituted nucleosides (2a) or (2b). The reaction of Step (A) is carried out in an inert solvent. Suitable inert solvents which may be used include tetrahydrofuran, acetone, dioxane, chloroform, dichloromethane, ether, nitrobenzene, dimethylsulfoxide, 1,2-dichloroethane, 1,2-dimethoxyethane, toluene and acetonitrile and/or any combination thereof. Preferably the inert solvent is anhydrous. Reaction temperatures can be in the range of 0° C. to 130° C. Most conveniently, the reaction is carried out by mixing the reactants between −5° C. and 40° C., followed by heating in a sealed vessel at 40° C. to 115° C. Preferably, the reaction is carried out by heating the reactants between 60° C. and 95° C. Reaction times usually vary from about one hour to about twenty-four hours, but generally a maximum yield is obtained between three and six hours.

As stated above, X is a halogen but most preferably is fluorine. The substituted organo-aluminum reagent may be selected from those of the formulae recited above. Particular reagents that may be used include di or trialkylaluminum, aluminum acetylacetonate, aluminum isopropoxide, tri-n-hexyl aluminum, triphenylaluminum, tribenzylaluminum or aluminum 3-acetylglycyrrhetate.

As used herein, the term "halogen" means fluoro, chloro, bromo or iodo. The substituents referred to in the terms "substituted aryl", "substituted phenoxy", "substituted phenyl" or "substituted thiophenyl" may be halogen, ($C_1$-$C_6$) alkyl or alkoxy.

Advantageously, the reagent used is HF dissolved in a suitable inert solvent at molar ratios of 0.01 to 15%. HF may be dissolved advantageously in dioxane, 1,2-dimethoxyethane or tetrahydrofuran.

In a preferred embodiment, particularly when a protected anhydronucleoside is used as a substrate, an increased yield and high level of purity is obtained when a mixed solvent system comprised of 30% pyridine and 70% hydrogen fluoride is used in the reaction mixture. Good results are also obtained when ammonium hydrogen difluoride or primary amine compounds are added to the reaction mixture.

As stated above, $R_1$ is selected from hydrogen, lower alkyl, halogen, olefinic, aryl and substituted aryl; $R_2$ is selected from hydrogen, lower alkyl, halogen, olefinic, aryl and substituted aryl; and $R_3$ is selected from hydrogen and halogen.

In preparing the preferred compound, FLT, a compound of formula I is produced wherein $R_1$ is selected from methyl, $R_2$ and $R_3$ are both hydrogen and X is fluorine. This compound has proven to possess excellent anti-HIV-1 activity.

Hydroxy-protecting groups P, which are known to those skilled in the art, are desirable because they prevent side reactions and provide increased yields in later steps of the reaction sequence. Suitable hydroxy-protecting groups may be, for example, acyl groups such as benzyloxy-carbonyl, benzhydryloxycarbonyl, trityloxycarbonyl, p-nitro-benzyloxycarbonyl, pivaloyl, and 2,2,2-trichloroethoxycarbonyl, aralkyl groups such as benzyl, benzhydryl, trityl or p-nitrobenzyl or triorganosilyl groups such as tri($C_1$–$C_6$) alkylsilyl (e.g., trimethylsilyl, triethylsilyl, triisopropylsilyl, isopropyldimethylsilyl, t-butyldimethylsilyl, methyldiisopropylsilyl or methyldi-t-butylsilyl), triarylsilyl (e.g., triphenylsilyl, tri-p-xylylsilyl) or triaralkylsilyl (e.g., tribenzylsilyl). Examples of these and other suitable hydroxy-protecting groups such as methanesulfonyl, alkyl sulfonyl, aryl sulfonyl and methods for their formation and removal are known in the art, see e.g., Protective Groups in Organic Synthesis, T. W. Greene, John Wiley & Sons, New York, 1981, Chapter 2. The hydroxy-protecting group selected is preferably one that is easily removable in Step (B) of the reaction process.

The reaction of Step (B) in which the protecting group P is trityl is best performed with p-toluenesulfonic acid in methyl alcohol at ambient temperature from about one hour to about twenty-four hours, but generally a maximum yield is obtained between eighteen and twenty four hours.

Upon further study of the specification and appended claims, further objects and advantages of this invention will become apparent to those skilled in the art.

This invention will be described in greater detail in conjunction with the following, non-limiting, specific examples.

EXAMPLE 1

5'-O-Triphenylmethyl-2',3'-dideoxy-3'-fluorothymidine

To a solution of 200 mg of 5'-O-triphenylmethyl-2'-deoxy-2,3'-anhydrothymidine in 5 ml of 1% HF-dioxane is added 0.11 ml of 2.0M trimethylaluminum in toluene. The vessel is sealed and heated at 50° C. for 24 hours. To the reaction is added 2 ml of water and 1 g of calcium carbonate followed by filtering. The filtrate is evaporated to a residue which is chromatographed on silica gel using 3:1 methylene chloride:acetone to afford 28.7 mg of 5'-O-Triphenylmethyl-2',3'-dideoxy-3'-fluorothymidine. (300 MHz $^1$H-NMR (DMSO,ppm): 11.40(s,1H), 7.50(s,1H), 7.45-7.25(m,15H), 6.23(d of d,1H), 5.43(d of d,1H), 4.24(d,1H), 3.35(d of d,1H), 3.20(d of d,1H), 2.6-2.3(m,2H), 1.43(s,3H)).

EXAMPLE 2

5'-O-Triphenylmethyl-2',3'-dideoxy-3'-fluorothymidine

To a solution of 1.0 g of 5'-O-triphenylmethyl-2'-deoxy-2,3'-anhydrothymidine in 13 ml of 3% HF-1,2-dimethoxyethane is added 3.2 ml of 1.0M triethylaluminum in hexane. The reaction vessel is sealed and heated at 60°-70° C. for 4 hours. The suspension is filtered through a 2 g pad of calcium carbonate. To the filtrate is added 5 ml of methyl alcohol followed by evaporation to give 520 mg of residue which is analyzed by high pressure liquid chromatography (HPLC) on silica gel using 3:1 methylene chloride-acetone and shown to contain 5'-O-Triphenylmethyl-2',3'-dideoxy-3'-fluorothymidine, (300 MHz $^1$H-NMR (DMSO,ppm): 11.40(s,1H), 7.50(s,1H), 7.45-7.25(m,15H), 6.23(d of d,1H), 5.43(d of d,1H), 4.24(d,1H), 3.35(d of d,1H), 3.20(d of d,1H), 2.6-2.3(m,2H), 1.43(s,3H)); 2',3'-dideoxy-3'-fluorothymidine, (300 MHz $^1$H-NMR (DMSO,ppm): 11.35(s,1H), 7.7(s,1H), 6.22(d of d,1H), 5.32(d of d,1H), 5.21(s,1H), 4.09-4.2(m,1H), 3.55-3.68(m,2H), 2.2-2.5(m,2H); m/e (EI)=244) and trityl alcohol.

EXAMPLE 3

2',3'-Dideoxy-3'-fluorothymidine

To a solution of 1 g of 5'-O-triphenyl-methyl-2'-deoxy-2,3'-anhydrothymidine in 13 ml of 3% HF-dimethoxyethane is added a solution of 1.3 ml of 2.4M diethylaluminumfluoride in heptane. The reaction vessel is sealed, heated at 60°-70° C. for 4 hours and filtered through a 2 g pad of calcium carbonate. To the filtrate is added 5 ml of methyl alcohol followed by evaporation to give 630 mg of a solid residue. The residue is analyzed by HPLC on silica gel using 3:1 methylene chloride:acetone and shown to be a mixture of 5'-O-Triphenylmethyl-2',3'-dideoxy-3'-fluorothymidine, (300 MHz $^1$H-NMR (DMSO,ppm): 11.40(s,1H), 7.50(s,1H), 7.45-7.25(m,15H), 6.23(d of d,1H), 5.43(d of d,1H), 4.24(d,1H), 3.35(d of d,1H), 3.20(d of d,1H), 2.6-2.3(m,2H), 1.43(s,3H),; 2',3'-dideoxy-3'-fluorothymidine, (300 MHz $^1$H-NMR (DMSO,ppm): 11.35(s,1H), 7.7(s,1H), 6.22(d of d,1H), 5.32(d of d,1H), 5.21(s,1H), 4.09-4.2(m,1H), 3.55-3.68(m,2H), 2.2-2.5(m,2H); m/e (EI)=244) and trityl alcohol. The residue is dissolved in methyl alcohol containing a catalytic amount of p-toluenesulfonic acid and stirred at room temperature for 24 hours, evaporated to a residue which is purified by silica gel chromatography using 3:1 methylene chloride:acetone to give 182 mg of the desired product.

EXAMPLE 4

5'-O-Triphenylmethyl-2',3'-dideoxy-3'-chlorothymidine

To a solution of 103.4 mg of 5'-O-triphenylmethyl-2'-deoxy-2,3'-anhydrothymidine in 5 ml of 3% HF-dioxane is added a solution of 55 μl of 1.0M diethylaluminum chloride. The reaction vessel is sealed and stirred at room temperature for 24 hours. To the mixture is added 2 ml of water and 1 g of calcium carbonate followed by filtering. The filtrate is evaporated to a residue which chromatographed on silica gel using 3:1 methylene chloride:acetone. Isolated from the fractions is 26 mg of 2',3'-dideoxy-3'-fluoro-thymidine and 52 mg of 5'-O-Triphenylmethyl-2',3'-dideoxy-3'-chlorothymidine.

EXAMPLE 5

5'-O-Methanesulfonyl-2',3'-dideoxy-3'-fluorothymidine

To a suspension of 579.5 mg of 5'-O-methanesulfonyl-2'-deoxy-2,3'-anhydrothymidine in 7 ml of 3% HF-1,2-dimethoxyethane is added a solution of 1.2 ml of 2.4M diethylaluminumfluoride in heptane. The reaction vessel is sealed and heated at 60°-70° C. for 24 hours. The mixture is filtered through a 1 g pad of calcium carbonate and the filtrate evaporated to give 343 mg of 5'-O-Methanesulfonyl-2',3'-dideoxy-3'-fluorothymidine. (300 MHz $^1$H-NMR (DMSO,ppm): 11.40(s,1H), 7.52(s,1H), 6.24(d of d,1H), 5.37(d of d,1H), 4.44(s,2H), 4.40(m,1H), 3.26(s,3H), 2.2-2.6(m,2H), 1.78(s,3H)).

EXAMPLE 6

2',3'-Dideoxy-3'-fluorothymidine

To a suspension of 200 mg of 2'-deoxy-2,3'-anhydrothymidine in 3 ml of 3% HF-dioxane is added 1.8 ml of 1.0M diethylaluminum fluoride. The vessel is sealed and heated at 80° C. for 24 hours. The suspension is filtered through a pad of calcium carbonate and the filtrate evaporated to give 20 mg of 2',3'-Dideoxy-3'-fluorothymidine. (300 MHz $^1$H-NMR (DMSO,ppm): 11.35(s,1H), 7.7(s,1H), 6.22(d of d,1H), 5.32(d of d,1H), 5.21(s,1H), 4.09–4.2(m,1H), 3.55–3.68(m,2H), 2.2–2.5(m,2H); m/e (EI)=244).

EXAMPLE 7

2',3'-Dideoxy-3'-fluorothymidine

To a solution of 1.5 g of 5'-O-triphenylmethyl-2'-deoxy-2,3'-anhydrothymidine in 15 ml of 3% HF-dimethoxyethane is added a solution of 4.8 ml of 1.0M tripropylaluminum in toluene. The reaction vessel is sealed and stirring continued at 65° C. for 4 hours. The mixture is filtered through a pad of calcium carbonate and the filtrate evaporated to a residue which is dissolved in methyl alcohol containing a catalytic amount of p-toluenesulfonic acid followed by stirring at room temperature for 24 hours. The reaction mixture is evaporated to a residue which is dissolved in hot 2-propanol then cooled to give 75 mg of 2',3'-Dideoxy-3'-fluorothymidine. (300 MHz $^1$H-NMR (DMSO,ppm): 11.35(s,1H), 7.7(s,1H), 6.22(d of d,1H), 5.32(d of d,1H), 5.21(s,1H), 4.09–4.2(m,1H), 3.55–3.68(m,2H), 2.2–2.5(m,2H); m/e (EI)=244).

EXAMPLE 8

2',3'-Dideoxy-3'-fluorothymidine

To a solution of 10.0 g of 5'-O-triphenylmethyl-2'-deoxy-2,3'-anhydrothymidine in 105 ml of 3% HF-dimethoxyethane while cooling in an ice bath is added 13.3 ml of 2.4M diethylaluminumfluoride in heptane dropwise over 5 minutes. The vessel is sealed and heated in an oil bath of 68° C. with stirring for 4 hours. The mixture is filtered through a pad of calcium carbonate and 20 ml of methyl alcohol added to the filtrate. The mixture is evaporated to a residue which is dissolved in 100 ml of methyl alcohol containing 1 g of p-toluenesulfonic acid and stirred at room temperature for 20 hours. The mixture is filtered and the filtrate evaporated to give 8.51 g of white solid which is dissolved in methylene chloride and chromatographed on silica gel by eluting with methylene chloride and 3:1 methylene chloride-acetone to give 1.78 g of the 2',3'-Dideoxy-3'-fluorothymidine. (300 MHz $^1$H-NMR (DMSO,ppm): 11.35(s,1H), 7.7(s,1H), 6.22(d of d,1H), 5.32(d of d,1H), 5.21(s,1H), 4.09–4.2(m,1H), 3.55–3.68(m,2H), 2.2–2.5(m,2H); m/e (EI)=244).

EXAMPLE 9

5'-O-Triphenylmethyl-2',3'-dideoxy-3'-fluorothymidine

To a solution of 1.04 g of 5'-O-triphenylmethyl-2'-deoxy-2,3'-anhydrothymidine in 10 ml of 3% HF-1,2-dimethoxyethane is added 712.62 mg of tri-t-butoxyaluminum. The vessel is sealed and heated at 65° C. for 4 hours. High pressure liquid chromatography on silica gel using 4:1 methylene chloride-acetone shows the presence of 5'-O-Triphenylmethyl-2',3'-dideoxy-3'-fluorothymidine.

EXAMPLE 10

2',3'-Dideoxy-3'fluorothymidine

To a suspension of 205.3 mg of 2'-deoxy-2,3'-anhydrothymidine in 5 ml of dimethoxyethane is added a solution of 1 ml of 1.0M diisopropylaluminum hydride in tetrahydrofuran. After stirring for 30 minutes, a solution of 5 ml of 3% HF-dimethoxyethane is added. The reaction vessel is closed and stirred at 70° C. for 17 hours. A 15 ml volume of methyl alcohol and 4 g of calcium carbonate is added followed by filtration. The filtrate is evaporated to a white solid which is purified by column chromatography on magnesium silicate using 4:1 methylene chloride-acetone to give 54.2 mg of 2',3'-dideoxy-3'-fluorothymidine.

EXAMPLE 11

2',3'-Dideoxy-3'-fluorothymidine

To a suspension of 2'-deoxy-2',3'-anhydrothymidine (523.4 mg, 2.34 mM) in 1,2-dimethoxyethane (2 ml) is added a solution of trihexylaluminum in heptane (25.1%, 1.03 ml). This mixture is stirred for 4.5 hours at room temperature and then heated to 65° C. for 15 minutes. A solution of 3% hydrogen fluoride/1,2-dimethoxyethane (7 ml) is added and the resultant mixture heated in a closed container at 65° C. for 24 hours. Upon addition of $H_2O$ (2 ml) and $CaCO_3$ (1 g) and adjusting the pH to neutrality with $Na_2CO_3$, the mixture is filtered. The filtrate is evaporated to yield a yellow solid which is recrystallized from 2-propanol to give 57 mg of 2',3'-dideoxy-3'-fluorothymidine. (300 MHz 1H-NMR (DMSO,ppm): 11.35(s,1H), 7.7(s,1H), 6.22(d of d,1H), 5.32(d of d,1H), 5.21(s,1H), 4.09–4.2(m,1H), 3.55–3.68(m,2H), 2.2–2.5(m,2H); m/e (EI)=244).

EXAMPLE 12

2',3'-Dideoxy-3'-fluorothymidine

To a suspension of 2'-deoxy-2',3'-anhydrothymidine (10 g, 45.4 mM) in a solution of 3% hydrogen fluoride/1,2-dimethoxyethane is added aluminum (acetylacetonate)$_3$ (22.1 g, 68.1 mM). The mixture is heated in a closed container at 90° C. for 20 hours. Upon addition of H2O (100 ml) and $CaCO_3$ (35 g), the suspension is filtered through hydrous magnesium silicate. The filtrate is evaporated and $H_2O$ (200 ml) added. To this is added activated carbon (2 g). The mixture is heated to reflux and filtered. The volume of the filtrate is evaporated by ⅔ and filtered again.

This final filtrate is evaporated to give 2',3'-dideoxy-3'-fluorothymidine (3.82 g). (300 MHz 1H-NMR (DMSO,ppm): 11.35(s,1H), 7.7(s,1H), 6.22(d of d,1H), 5.32(d of d,1H), 5.21(s,1H), 4.09–4.2(m,1H), 3.55–3.68(m,2H), 2.2–2.5(m,2H); m/e (EI)=244).

EXAMPLE 13

2',3'-Dideoxy-3'-fluorothymidine

To a solution of 5'-O-acetyl-2'-deoxy-2,3'-anhydrothymidine (204 mg, 0.72 mM) in 3% hydrogen fluoride/1,2-dimethoxyethane is added a solution of diethylaluminum fluoride/heptane (2.4M, 0.46 ml). The mixture is heated in a closed container at 58° C. for 24 hours upon which $CaCO_3$ (2 g) is added. The pH is adjusted to neutrality using $Na_2CO_3$ and the mixture is filtered. The filtrate is evaporated and the residue dissolved in a mixture of 3:1 $CH_2Cl_2$-acetone and filtered through a pad of silica gel. The filtrate is evaporated to give 5'-O- acetyl-2',3'-dideoxy-3'-fluorothymidine (160.5 mg). This material is dissolved in methanol (5 ml) and K$_2$CO$_3$ (225 mg) is added. After stirring 10 minutes, the solution is filtered and the filtrate evaporated. The residue is slurried in acetone and filtered. Evaporation of the filtrate produces 2',3'-dideoxy-3'-fluorothymidine (121 mg). (300 MHz $^1$H-NMR (DMSO,ppm): 11.35(s,1H), 7.7(s,1H), 6.22(d of d,1H), 5.32(d of d,1H), 5.21(s,1H), 4.09–4.2(m,1H), 3.55–3.68(m,2H), 2.2–2.5(m,2H); m/e (EI)=244).

EXAMPLE 14

5'-O-Methanesulfonyl-2',3'-dideoxy-3'-fluorothymidine

To a 600 ml stirred clave charge 10 g of 5'-O-methanesulfonyl-2'-deoxy-2,3'-anhydrothymidine, (280 ml), dioxane (42.9 ml) of 10% HF in dioxane and tri-n-hexyl aluminum. The clave is sealed and the reaction is allowed to stir at 77°–84° C. for 3 hours, 14 hours at ambient temperature then 77°–84° C. for 3 hours. After recooling to ambient temperature, the reaction is poured into calcium carbonate (30 g) in H$_2$O (50 ml) and the resulting slurry is stirred for 30 minutes and clarified through silica gel (10 g). The filtrate is concentrated to about 50 ml, H$_2$O (25 ml) is added and concentration continued to 25 ml. The resulting solids are collected by filtration and dried to afford 6.59 g (62%) of 5'-O-methanesulfonyl-2',3'-dideoxy-3'-fluorothymidine as an off-white solid.

EXAMPLE 15

5'-O-Triphenylmethyl-2',3'-dideoxy-3'-fluorothymidine

A mixture of 0.2 g of 5'-O-triphenylmethyl-2'-deoxy-2,3'-anhydrothymidine and 0.2 g of aluminum acetylacetonate is slurried in 5.2 ml of dioxane. While stirring, 1.5 ml of 10% hydrogen fluoride in dioxane is added. The mixture is heated at 50°–53° C. for 19 hours, cooled, 1 ml of water added followed by 0.8 g of calcium carbonate and methylene chloride. The mixture is filtered, the cake washed with acetone and the separated organic layer evaporated to give 0.15 g of 5'-O-triphenylmethyl-2',3'-dideoxy-3'-fluorothymidine.

EXAMPLE 16

5'-O-Triphenylmethyl-2',3'-dideoxy-3'-fluorothymidine

A mixture of 0.24 g of 5'-O-triphenylmethyl-2'-deoxy-2,3'-anhydrothymidine and 0.22 g of aluminum isopropoxide in 4.28 g of dimethoxyethane is treated with 10% hydrogen fluoride. The mixture is heated in an oil bath of 40°–45° C. for 22 hours. The mixture is cooled, 0.2 ml of water and 1.0 g of calcium carbonate added. The mixture is filtered and the cake washed with acetone and mothylene chloride. The filtrate is evaporated to give 0.16 g of 5'-O-triphenylmethyl-2',-3'-dideoxy-3'-fluorothymidine.

EXAMPLE 17

5'-O-Methanesulfonyl-2',3'-dideoxy-3'-fluorothymidine

To a stirred autoclave charge 10 g of 5'-O-methanesulfonyl-2'-deoxy-2,3'-anhydrothymidine, 20.3 g of aluminum isopropoxide, 7.3 ml of 10% HF in dioxane and 128 ml of dioxane. The clave is sealed and stirred and heated at approximately 90° C. for 3 hours. After cooling to ambient temperature the mixture is drowned into a mixture of calcium carbonate (40 g) and water (50 ml). The slurry is stirred for about 30 minutes and clarified through a Buchner funnel. The cake is washed with acetone (4×25 ml). The solution is evaporated to dryness and slurried with acetone (100 ml). The insolubles are filtered off and the solution evaporated to dryness to give 9.05 g of 5'-O-Methanesulfonyl-2',3'-dideoxy-3'-fluorothymidine as a solid.

EXAMPLE 18

5'-O-Methanesulfonyl-2',3'-dideoxy-3'-fluorothymidine

To an autoclave charge 5.0 g of 5'-O-methanesulfonyl-2'-deoxy-2',3'-anhydrothymidine, 5.9 g aluminum acetylacetonate, 85 ml of dioxane and 20 ml of 10% HF in dioxane. The bath is heated at 100°–108° C. for 1¼ hour, cooled to room temperature and diluted with 10 ml dioxane, 25 ml of water, 50 ml of acetone and 8.0 g of calcium carbonate are added and stirred for 30 minutes. The mixture is clarified, the cake washed with acetone and the filtrate evaporated to dryness to yield 6.0 g of 5'-O-methanesulfonyl-2,3'-dideoxy-3'-fluorothymidine.

EXAMPLE 19

5'-O-Methanesulfonyl-2',3'-dideoxy-3'-fluorothymidine

A mixture of 5.0 g of 5'-O-methanesulfonyl-2'-deoxy-2,3'-anhydrothymidine, 16.1 g of aluminum acetylacetonate and 5.0 ml of (30% pyridine −70% hydrogen fluoride) in 100 ml of dioxane is heated in a clave at 88°–93° C. for 3 hours. The clave is cooled to room temperature and the contents poured into 50 ml of water containing 15 g of calcium carbonate. An additional 21 g of calcium carbonate is added with continued stirring. The resulting pH is 5. The mixture is filtered through diatomaceous earth and the cake washed with acetone. The filtrate is evaporated several times with acetone to give a residue which is dissolved in 100 ml of acetone and filtered through cotton. The filtrate is evaporated and the residue vacuum dried to give 4.4 g of the desired product.

EXAMPLE 20

5'-O-Methanesulfonyl-2',3'-dideoxy-3'-fluorothymidine

To a stirred autoclave charge 25 g of 5'-O-methanesulfonyl-2'-deoxy-2,3'-anhydrothymidine, 83 ml of 2M trihexyl aluminum in dioxane, 98 ml of dioxane and 19 ml of a mixture of 70% hydrogen fluoride and 30% pyridine. The clave is sealed and heated to 85°–90° C. and held at approximately 90° C. for 3 hours. The batch is cooled to room temperature and drowned in a mixture of calcium carbonate (40 g) in water (100 ml). The mixture is stirred for about 15 minutes, clarified and the cake washed with acetone (4×25 ml). The solution is partially concentrated under vacuum, water is added (200 ml) and the solution concentrated further. The mixture is cooled to 0°–5° C., filtered, washed with cold water (about 45 ml) and dried to yield 22.2 g of product.

EXAMPLE 21

5'-O-Methanesulfonyl-2',3'-dideoxy-3'-fluorothymidine

To a stirred autoclave is charged 1,000 g 5'-O-methanesulfonyl-2'-deoxy-2,3'-anhydrothymidine, 6,000 ml of 1,4-dioxane, 1,180 g of aluminum acetylacetonate, 100 g of ammonium hydrogen difluoride and 4,000 ml of a 10% solution of hydrogen fluoride in dioxane. The clave is sealed and stirred and heated at 85°–90° C. for 3 hours. The batch is cooled to 20°–30° and drowned into a slurry of calcium carbonate (2,000 g) in water (10,000 ml). The slurry is stirred for 15-30 minutes and the solids removed by filtration. The filter cake is washed with acetone (7,500 ml) and the combined filtrate and wash is concentrated under reduced pressure to a volume of 6-7.5 liters. Then water (2,000 ml) is added and the solution is concentrated further to 7-7.5 liters. The mixture is cooled to 0°-5° C. and stirred at 0°-5° C. for 30-60 minutes. The product is filtered, washed with cold water (1,500 ml) and dried to yield 762 g of 5'-O-methanesulfonyl-2',3'-dideoxy-3'-fluorothymidine.

EXAMPLE 22

5'-O-Methanesulfonyl-2',3'-dideoxy-3'-fluorothymidine

To a 300 ml stirred autoclave charge 10 g of 5'-O-methanesulfonyl-2'-deoxy-2',3'-anhydrothymidine, 19.3 g of aluminum isopropoxide, and 90 ml of dioxane. After sealing the clave, 10.4 ml of a 30% pyridine-70% hydrogen fluoride mixture is added with an exotherm to about 58° C., the reaction is heated to 90° C. and stirred at 90° C. for 3 hours. Upon cooling to room temperature, the reaction is diluted with H$_2$O (50 ml) and treated with calcium carbonate (40 g). Following the 20 minute stir period, the reaction is filtered and the solids washed with acetone. The combined filtrates are concentrated to a semi-solid, acetone (50 ml) is added and the solution is stripped to dryness. The resulting solids are dried to afford 10.8 g of the product.

We claim:

1. In a process for preparing a compound of the Formula I:

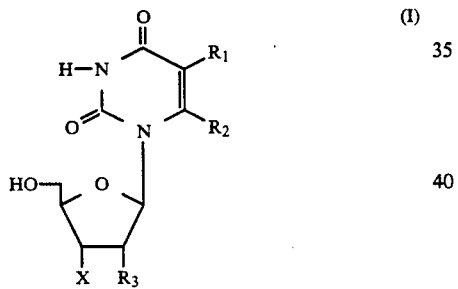

wherein R$_1$ and R$_2$ may be the same or different and are selected from the group consisting of hydrogen, lower alkyl and halogen; R$_3$ is selected from the group consisting of hydrogen and halogen; and X is a halogen; the improvement which comprises the steps of:

(a) mixing a compound of the formula:

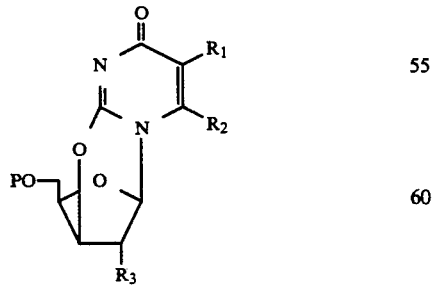

wherein P is selected from the group consisting of hydrogen, triphenylmethyl, methoxytriphenylmethyl, acetyl, pivaloyl, methanesulfonyl or trialkylsilyl with a reagent of the formula H-X wherein X is a halogen; in the presence of a reagent of the formula:

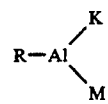

wherein R is selected from the group consisting of (C$_1$-C$_{12}$) branched or unbranched alkyl, (C$_1$-C$_{12}$) branched or unbranched alkoxy, phenyl, substituted phenyl, carboxylate, benzyl, enolate, carbonyl, b-diketonate, (C$_1$-C$_{12}$) branched or unbranched thioalkyl, thiophenyl or substituted thiophenyl wherein the substituting moiety in the aforesaid substituted phenyl or substituted thiophenyl is selected from halogen, (C$_1$-C$_6$) alkyl and alkoxy; K and M may be the same or different and are selected from the group consisting of R and hydrogen, in an inert organic solvent, (b) heating said compound and reagents at 40°-115° C. for about one to 24 hours to produce a compound of the formula:

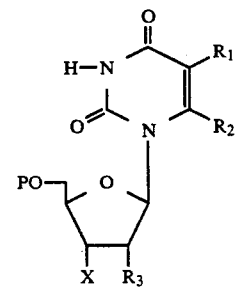

and, where P is other than hydrogen, (c) removing said protecting group.

2. In a process for preparing a compound of the formula II:

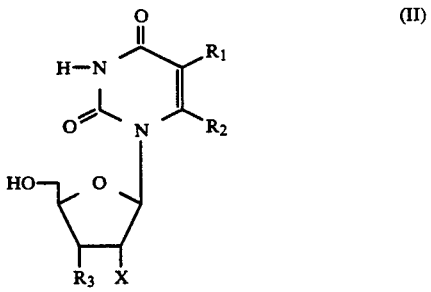

wherein R$_1$ and R$_2$ may be the same or different and are selected from the group consisting of hydrogen, lower alkyl and halogen; R$_3$ is selected from the group consisting of hydrogen and halogen; and X is a halogen; the improvement which comprises the steps of:

(a) mixing a compound of the formula:

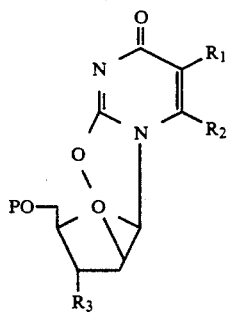

wherein P is hydrogen or a protecting group selected from the group consisting of triphenylmethyl, methoxytriphenylmethyl, acetyl, pivaloyl, methanesulfonyl or trialkylsilyl with a reagent of the formula H-X wherein X is a halogen; in the presence of a reagent of the formula:

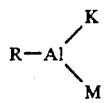

wherein R is selected from the group consisting of ($C_1$–$C_{12}$) branched or unbranched alkyl, ($C_1$–$C_{12}$) branched or unbranched alkoxy, phenyl, substituted phenyl, hydrogen, carboxylate, benzyl, enolate, carbonyl, ($C_1$–$C_{12}$) branched or unbranched thioalkyl, thiophenyl or substituted thiophenyl wherein the substituting moiety in the aforesaid substituted phenyl or substituted thiophenyl is selected from halogen, ($C_1$–$C_6$) alkyl and alkoxy, K and M may be the same or different and are selected from the group consisting of R and hydrogen, in an inert organic solvent;

(b) heating said compound and reagents at 40°–115° C. for about one to 24 hours to produce a compound of the formula:

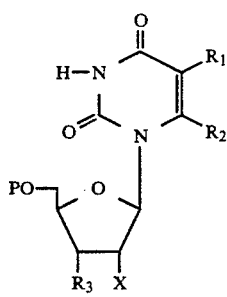

and, where P is other than hydrogen, (c) removing said protecting group.

3. A process according to claim 1 in which the reagent H-X is HF.

4. A process according to claim 2 in which the reagent H-X is HF.

5. A process according to claim 1 in which the reagent

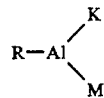

is trimethylaluminum wherein R, K and M are methyl.

6. A process according to claim 2 in which the reagent

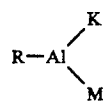

is trimethylaluminum wherein R, K and M are methyl.

7. A process according to claim 1 in which the reagent

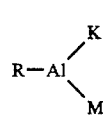

is triethylaluminum wherein R, K and M are ethyl.

8. A process according to claim 2 in which the reagent

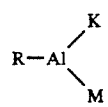

is triethylaluminum wherein R, K and M are ethyl.

9. A process according to claim 1 in which the reagent

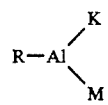

is tripropylaluminum wherein R, K and M are each propyl.

10. A process according to claim 2 in which the reagent

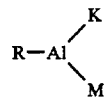

is tripropylaluminum wherein R, K and M are each propyl.

11. A process according to claim 1 in which the reagent

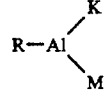

is tri-t-butoxyaluminum wherein R, K and M are each t-butoxy.

12. A process according to claim 2 in which the reagent

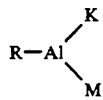

is tri-t-butoxyaluminum wherein R, K and M are each t-butoxy.

13. A process according to claim 1 in which the reagent

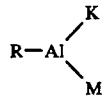

is diisobutylaluminum hydride wherein R and M are isobutyl and K is hydrogen.

14. A process according to claim 2 in which the reagent

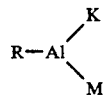

is diisobutylaluminum hydride wherein R and M are isobutyl and K is hydrogen.

15. A process according to claim 1 in which the reagent

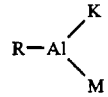

is triphenylaluminum wherein R, K and M are each phenyl.

16. A process according to claim 2 in which the reagent

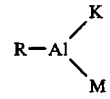

is triphenylaluminum wherein R, K and M are each phenyl.

17. A process according to claim 1 in which the reagent

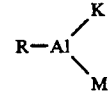

is tribenzylaluminum wherein R, K and M are each benzyl.

18. A process according to claim 2 in which the reagent

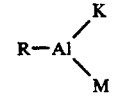

is tribenzylaluminum wherein R, K and M are each benzyl.

19. A process according to claim 1 in which the reagent

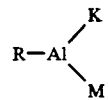

is aluminum isopropoxide wherein R, K and M are each isopropoxy.

20. A process according to claim 2 in which the reagent

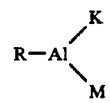

is aluminum isopropoxide wherein R, K and M are each isopropoxy.

21. A process according to claim 1 in which the reagent

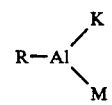

is aluminum ethoxide wherein R, K and M are each ethoxy.

22. A process according to claim 2 in which the reagent

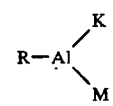

is aluminum ethoxide wherein R, K and M are each ethoxy.

23. A process according to claim 1 in which the reagent

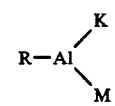

is aluminum acetylacetonate wherein R, K and M are each 2,4-pentanedionate.

24. A process according to claim 1 in which the reagent

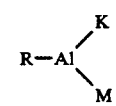

is aluminum acetylacetonate wherein R, K and M are each 2,4-pentanedionate.

25. A process according to claim 1 in which the reagent

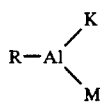

is aluminum 3-acetylglycyrrhetate wherein R, K and M are each 3-acetylglycyrrhetate.

26. A process according to claim 2 in which the reagent

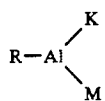

is aluminum 3-acetylglycyrrhetate wherein R, K and M are each 3-acetylglycyrrhetate.

27. A process according to claim 1 in which the reagent

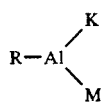

is n-trihexylaluminum wherein R, K and M are each n-hexyl.

28. A process according to claim 2 in which the reagent

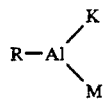

is n-trihexylaluminum wherein R, K and M are each n-hexyl.

29. A process according to claim 1 in which the inert organic solvent is selected from dioxane, tetrahydrofuran or dimethoxyethane.

30. A process according to claim 2 in which the inert organic solvent is selected from dioxane, tetrahydrofuran or dimethoxyethane.

31. A process according to claim 1 in which the preferred temperature range is 60°–95° C.

32. A process according to claim 2 in which the preferred temperature range is 60°–95° C.

33. A process according to claim 1 in which the reagent HF is in a concentration of 0.01 to 15% in an ether solvent.

34. A process according to claim 2 in which the reagent HF is in a concentration of 0.01 to 15% in an ether solvent.

35. A process according to claim 1 in which the reagent HX is HF which is mixed with pyridine.

36. A process according to claim 2 in which the reagent HX is HF which is mixed with pyridine.

37. A process according to claim 35 in which the HF/pyridine concentration ratio is 70% HF to 30% pyridine.

38. A process according to claim 36 in which the HF/pyridine concentration ratio is 70% HF to 30% pyridine.

39. A process according to claim 1 in which ammonium hydrogen difluoride is added to the reaction mixture.

40. A process according to claim 2 in which ammonium hydrogen difluoride is added to the reaction mixture.

* * * * *